United States Patent [19]
Darby

[11] Patent Number: 6,021,780
[45] Date of Patent: Feb. 8, 2000

[54] IMMOBILIZATION BRACE WITH OVERLAPPING VENTILATION PORTS WITHIN SEMI-FLEXIBLE BOOT AND FOAM SHEET MATERIAL LINER

[75] Inventor: H. Darrel Darby, Huntington, W. Va.

[73] Assignee: Darco International, Inc., Huntington, W. Va.

[21] Appl. No.: 09/112,239

[22] Filed: Jul. 9, 1998

[51] Int. Cl.⁷ ...................................................... A61F 5/37
[52] U.S. Cl. .............................. 128/882; 602/23; 602/27
[58] Field of Search .................................. 128/869, 882; 602/5, 12, 13, 23, 27, 65

[56] References Cited

U.S. PATENT DOCUMENTS 4,478,214 10/1984 Lamont ................................... 128/882
5,370,133 12/1994 Darby et al. .
5,425,701 6/1995 Oster ......................................... 602/23

Primary Examiner—Michael A. Brown
Attorney, Agent, or Firm—Sughrue, Mion, Zinn, MacPeak & Seas, PLLC

[57] ABSTRACT

A lower leg, ankle and foot immobilization brace utilizing a semi-flexible open front boot fixed to the top of a walker sole with a plurality of spaced ventilation ports in the boot carries a foam liner within the boot sized to surround the lower leg, ankle, foot and dorsum of the user's limb. Spaced closures spanning the open front boot apply gentle and focal compression to the foam liner encased limb. Appropriate elongated ventilation ports within the foam liner overlap a plurality of spaced ventilation ports in the boot to facilitate cooling air flow directly from the boot exterior to the skin of the user's limb encased by the foam liner.

14 Claims, 3 Drawing Sheets

IMMOBILIZATION BRACE WITH OVERLAPPING VENTILATION PORTS WITHIN SEMI-FLEXIBLE BOOT AND FOAM SHEET MATERIAL LINER

FIELD OF THE INVENTION

The present invention relates to a semi-flexible molded polyurethane boot which surrounds a breathable open pore foam inner liner forming a short length or regular walker, with the boot provided with adjustable leverage-type pawl and rack closures for general compression and focal compression of the brace, and more particularly to a ventilation system consisting of overlapping ventilation ports or windows within the dorsum of the boot and the boot upper which overlap ventilation ports or windows within the liner opening directly to the skin of the leg and foot of the patient wearing the same.

BACKGROUND OF THE INVENTION

This invention is directed to an improvement within a short length or regular walker in the form of an immobilization brace with uniform adjustable compression, which is the subject of U.S. Pat. No. 5,370,133 issued Dec. 6, 1994, and assigned to the common assignee. Such brace consisted of a semi-flexible molded polyurethane boot closed at the rear and sides and open at the front, surrounding a preferably breathable open pore foam inner liner which covers the lower leg, ankle and foot of a patient. A boot front portion is fixed to a walking sole having a minimal rocker effect and of minimal thickness. The foot portion of the boot has a rounded heel counter and a contoured foot bed with a shock absorbing foam insole within the boot portion to recess pad the plantar surface of the sole. The dorsum of the boot and the boot upper are provided with spaced ventilation ports or windows to ventilate the leg, ankle and foot of the user through the porous open foam liner. The dorsum of the boot and the boot upper are provided with spaced, adjustable, leverage-type closures to provide adjustable general compression and focal compression to assure a proper fit of the brace and to reduce edema induced swelling throughout the leg, ankle and foot. The boot upper and boot foot portions may be separately formed of two parts hinged together, but preferably locked to prevent fore and aft rotation of the boot upper relative to the foot portion fixed to the sole. In such immobilization brace assemblies, patients enjoy the same hard shell, circumferential protection as a plaster or like cast, while additionally, unlike casts, the immobilization brace of U.S. Pat. No. 5,370,133 does not loose its effectiveness as edema subsides and muscles begin to atrophy. Further, the leverage fasteners, similar to ski boot buckles being attached directly to the molded plastic shell, provide controlled compression and immobilization throughout the healing process without becoming a tangled mess like hook and loop velcro closures. As the shape of the lower leg changes during the healing process, the outer shell portion moves to conform and reconform one click at a time.

However, during use, the patients wearing the immobilization brace of the prior patent express a major complaint that such immobilization assembly is extremely hot in spite of the ports or windows within the molded plastic outer boot dorsum and upper portions.

It is therefore a primary object of the present invention to provide such immobilization brace assemblies with air ventilation ports or windows appropriately carried by the inner liner which extends therethrough, which are preferably of elongated form so as to cross and overlap a series of spaced ventilation ports within the molded plastic outer boot to readily cause exterior air to penetrate directly to the skin of the user and allow body heat to be released without materially adversely affecting the snug fit of the boot and liner assembly about the leg, ankle and foot of the user.

It is a further object of the invention to provide the liner component of the assembly with loose woven, open mesh material sewn over the ventilation ports within the liner to keep the elongated ports within the liner from spreading out of shape, while further keeping the soft tissue of the user from pushing through the liner ports, particularly in the case of edema.

Other advantages of the present invention will become apparent from the description of the preferred embodiment and from the accompanying drawings.

SUMMARY OF THE INVENTION

The invention is directed to an improvement within a lower leg, ankle and foot immobilization brace in the form of a leg walker and a ventilation system improvement within the liner component, with the walker formed principally of an injection molded plastic material outer boot to provide controlled, uniform compression of the foot, ankle and leg covered by the brace, while at the same time immobilizing those aspects of the lower limb subject to surgery or trauma. The immobilization brace with compression effected by adjustable, leverage type pawl and rack closures or their equivalents to effect readily manually adjustable, general compression closure of the brace. The dorsum of the boot and the boot upper are provided with ventilation ports to ventilate the leg, ankle and foot of the user. A breathable foam inner liner is provided with elongated ventilation ports which are preferably at an angle to intersectingly overlap the ventilation ports within the molded plastic boot upper and/or dorsum. The ventilation ports within the liner act as cooling air passages to permit cooling air entering from the exterior of the brace through the ventilation ports within the outer boot to contact directly the skin of the user along surfaces of the leg and/or foot. In addition to the cooling effect body heat is released from the leg and foot through the elongated ventilation ports. The ventilation ports within the boot upper and the dorsum of the boot may extend generally horizontally as a spaced vertical series across the rear of the boot upper, or as paired rows of vertically spaced ports on opposite sides of the boot upper. The ventilation ports within the dorsum may be of elongated form or square, spaced from each other and extending generally horizontal along the length of the dorsum forward of the boot upper. Preferably, an open mesh porous cloth covers the ventilation ports within the liner. The edges of the ventilation ports within the liner may be bound by stitches, with an underlying binding tape or ribbon to prevent slot enlargement during use without materially affecting the flow of air through the mesh covered ventilation ports within the liner.

DESCRIPTION OF THE PREFERRED EMBODIMENT

Figure 1:
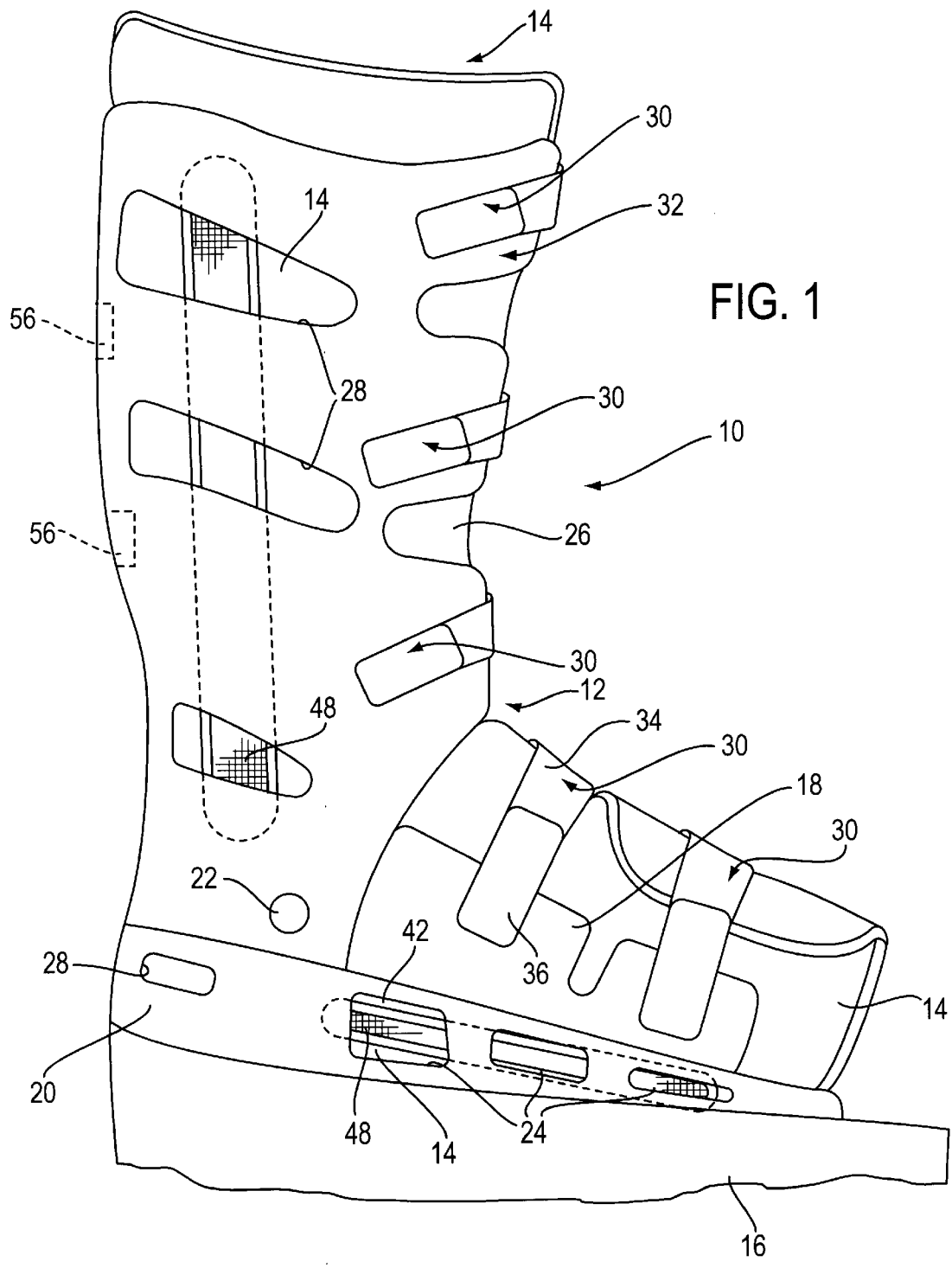
FIG. 1 is a side elevational view of a short length leg walker forming a preferred embodiment of the invention.

Referring to the drawings, a lower leg, ankle and foot, short length leg walker or immobilization brace assembly is indicated generally at 10 and forms a preferred embodiment of the invention. The assembly is similar to that of U.S. Pat. No. 5,370,133 and incorporates two principal components, a semi-flexible boot indicated generally at 12, preferably formed of an injection molded material such as polyurethane and surrounding and supporting the second principal component, an internal breathable foam liner indicated generally at 14. The content of U.S. Pat. No. 5,370,133 is incorporated herein by specific reference thereto.

Like the referred to patent, brace 10 provides controlled, uniform compression of the foot, ankle and leg, while simultaneously immobilizing those body parts of the user or wearer. The outer boot 12 of brace 10 is provided with a walking sole indicated generally at 16, all in accordance with the referred to patent. The sole structure 16 may be identical to that of the sole within the referred to patent. Further, the walker has an open toe area forward of the boot foot portion 18, and at the rear of the foot portion 18, the boot 12 has a boot upper indicated generally at 32 hinged to the boot foot portion 18 by means of relatively large size rivets 22 at opposite sides of the boot. The boot counter 20 extends about the rear of the immobilization brace 10. A series of ventilation ports or windows 24 are formed within the foot portion 18 of the boot 12, in this case there being three in number on each side of the boot which extend generally horizontal and are elongated horizontally and spaced from each other. The upper 32 is generally C-shaped in horizontal cross-section, being vertically elongated and having a frontal opening indicated generally at 26. Preferably, the upper portion 32 of the boot 12 is constructed of slightly less rigid material than the foot portion 18, providing sufficient rigidity through the long axis of the upper while being semi-flexible and allowing the entire upper of the boot to conform to the leg of the user. Unlike in the immobilization brace of the referred to patent, the ventilation ports or windows 24 within the boot upper 32 are in the form of two rows, one row each to opposite sides of the upper, being generally parallel to each other and spaced vertically while extending at a slight angle to the horizontal, as seen in the single row of ports or slots 28 on the right side of the boot 12, FIG. 1. The ventilation ports 28 are elongated, that is their length is in excess of their height. Such may be readily varied as desired. As seen in FIG. 1, the top of the liner 14 extends above the top of the molded plastic boot 12. In similar fashion to U.S. Pat. No. 5,370,133, the boot upper 32 as well as the foot portion 18 is provided with pawl and rack leverage closures or fasteners indicated generally at 30 which couple opposite sides of the boot upper 32. In like fashion, the pawl and rack leverage closures or fasteners 30 associated with the immobilization brace 10 for adjustably coupling the opposite sides of the foot portion 18 of the boot 12 are identical to those provided to the boot upper 32. They are comprised principally of a flexible molded plastic strap indicated generally at 34, and a pivoted buckle indicated generally at 36. The details of the same may be appreciated from the content of U.S. Pat. No. 5,370,133. In drawing FIGS. 1 and 2, the exterior surfaces of liner 14 may be seen through the open ventilation ports or windows 24, 28.

Figure 2:
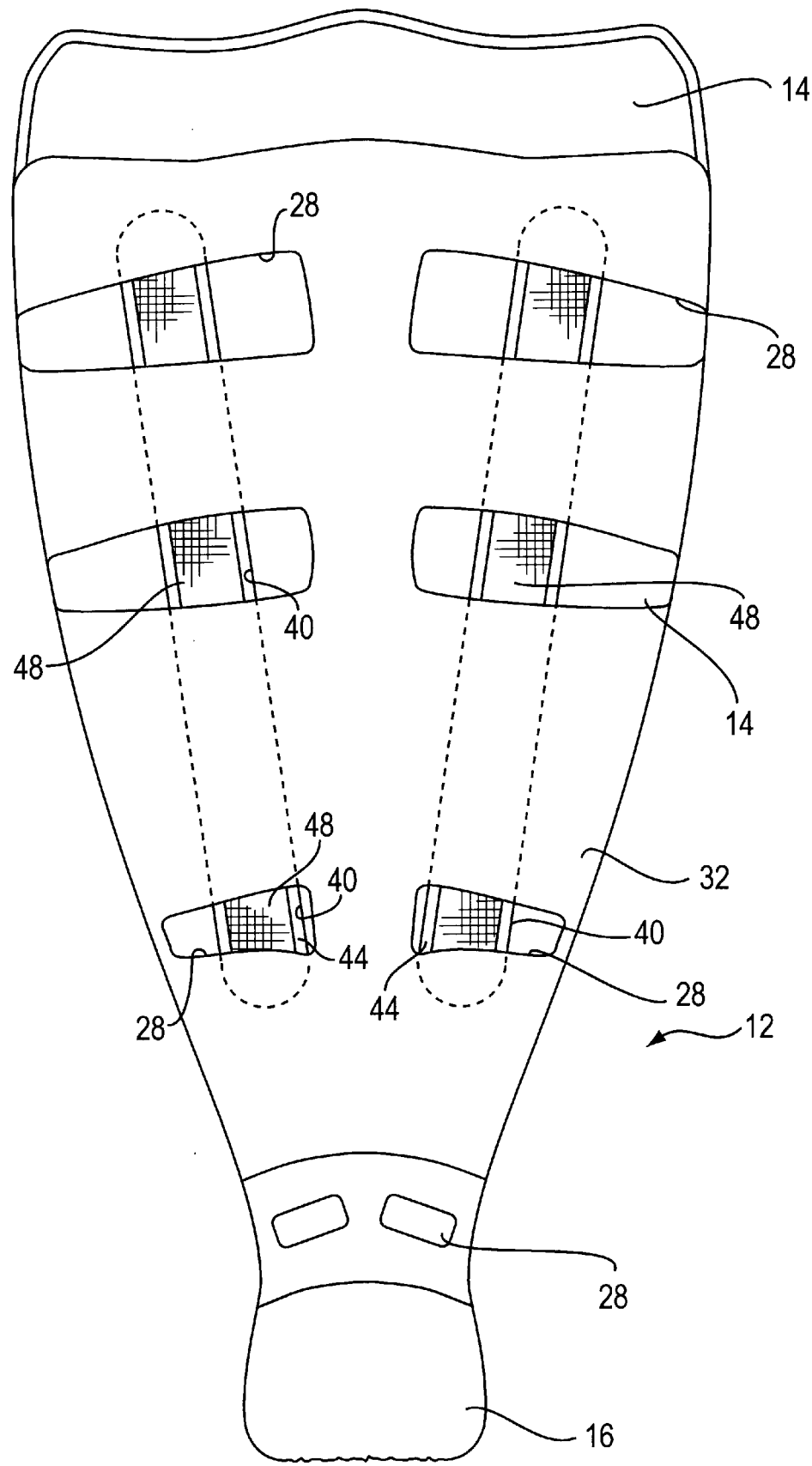
FIG. 2 is a rear elevational view of the short length leg walker of FIG. 1.
Figure 3:
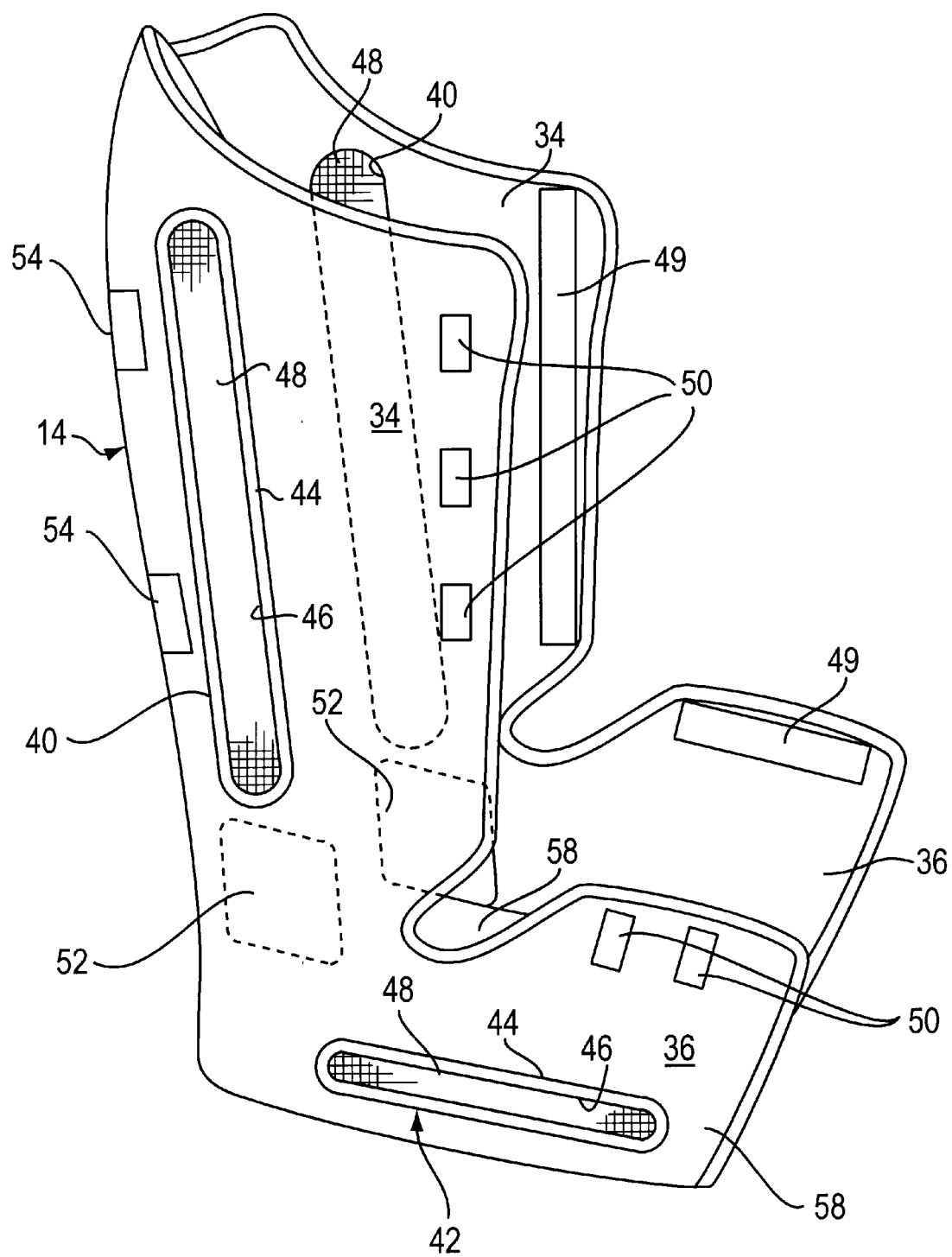
FIG. 3 is a rear, left side perspective view of the liner forming a key element of the short length leg walker of FIGS. 1 and 2, the opposite side being a mirror image thereof.

Turning to FIG. 3, a perspective view of liner 14, it is apparent that the liner 14 is similar to that of FIG. 2 of U.S. Pat. No. 5,370,133 and may be identical thereto with the exception of the improvement provided by ventilation ports or windows provided within this member of the assembly 10. Liner 14 of FIG. 3 is preferably of a breathable, open pore foam sheet molded to have a thickness of about 1 inch and being cut and edge sealed or of ports sewn together to form an L-shaped enclosure in side elevation, being closed on the bottom rear and sides, but open at the front, to readily and freely receive the lower lege, ankle and foot of the user. As such, liner sides 34 correspondingly received within boot upper 32 wrap about the leg above the ankle, with one flap underlying the opposite flap. Similar to U.S. Pat. No. 5,370, 133, the open pore foam sheet from which the liner 14 is formed is covered on opposite faces by a woven sheet material as outer and inner layers thereof and VELCRO® hook material strips 49 are mounted to an interior surface along a side edge of one of the undersides 34 so as to frictionally and mechanically engage the cloth surface on the outside of the opposite liner side 34 to maintain the foam liner releasably locked closed about the leg of the user and conforming thereto, or may attach to loop type VELCRO® strips or pads 50 fixed to such cloth surface at spaced positions.

Similarly, for the dorsum of the foot of the user, dorsum flaps 36 of the liner 14 wrap about the exterior of the foot of the user, and overlapping flaps 36 may use second VELCRO® hook-type fastener material strips or straps 49, 50 similar to the arrangement for releasably locking the overlapping edges of the sides 34 of the liner, all in accordance with U.S. Pat. No. 5,370,133. Thus, a releasable VELCRO® hook and loop type fastening system is achieved in the area of the dorsum of the foot and the shin of the user to envelope the leg, ankle and foot in a protective, breathable, soft, compressible foam envelope.

The above description of the liner 14 follows generally that of U.S. Pat. No. 5,370,133.

A principal aspect of the present invention consists in forming suitable ventilation ports or windows 40 within the opposite sides 34 of liner 14, FIG. 3, and ventilation ports or windows 42 within opposite flaps 36 of that member. The ports 40 are generally vertical or near vertical, of extended length and of given width to permit body heat to escape and air to pass freely through the ports or windows 40 which open directly to the skin of the user's leg above the ankle and below the knee on opposite sides of the assembly 10. In contrast, the ports or windows 42 within the flaps 36 are nearly horizontal, of lesser length, although elongated, so as to overlappingly open to the various ventilation ports 24 within the boot 12. The edges of the ventilation ports or windows 40, 42 preferably have a ribbon or binding 44 sewn by way of stitches 46 to the liner 14 to prevent raveling of the outer fabric and inner fabric covering of the porous foam liner 14 at the port edges. Additionally, it is preferred that a loose woven material 48, which is highly porous, functions as cover for the ventilation ports or windows 40, 42 over the under surface of the ventilation ports or windows, next to the skin. Such loose woven or open mesh material extending over the open ventilation ports or windows within the liner 14 prevents the soft tissue of the user's limb from pushing through the ventilation openings, particularly in the case of edema. Such loose woven material 48 is so porous as not to interfere with the escape of heat from the foot and leg through ventilation ports or windows 40, 42, and also allows the air to circulate through the vented area via overlapping ventilation ports within the molded plastic boot 12.

As seen in FIGS. 1 and 2, the location of the near vertical ports 40 and the near horizontal ports 42 within liner 14 is such when the liner 14 is inserted within the boot 12 to form the assembly 10 and the lengths of the ports overlap each other in part or whole and extend beyond the row of vertical ventilation ports 28 within the upper 32 of the boot. Respective ventilation ports of the boot component of the brace thus lie across and intersect the row of ventilation ports or windows 24 within the foot portion 18 of the outer boot 12. As seen in FIG. 2, the nearly vertical ventilation ports or windows 40 within the opposite sides 34 of the liner do not extend the full height of the boot 12 so as to intersect the lowermost ventilation ports 28 for boot 12, although such could be readily accomplished.

The combination of the two major components of the boot, the liner 14 in its modified form from U.S. Pat. No. 5,370,133 and the molded plastic boot 12 create an excellent skin ventilation system along both sides of the foot, ankle and leg of the user, with direct and virtually unimpeded contact between the ambient air and the surface of the skin of the user without compromising the compressive protective nature of the immobilization device 10 and the protection afforded the leg, ankle and foot against torsion while preventing dorsal flexion and plantar flexion inversion and eversion of the foot and ankle joints.

While changes and modifications have been discussed to some degree with respect to the illustrated embodiment, it should be apparent that other changes may be made to the immobilization brace without departing from the scope of the invention, as set forth within U.S. Pat. No. 5,370,133, of which this application constitutes an improvement. In that respect, while the boot upper 32 and the foot portion 18 have been illustrated as including single rows of ventilation ports to opposite sides of the outer boot 12, the size, number and configuration of the ventilation ports may be readily varied. For instance, multiple rows of ventilation ports may be provided within each component of the molded plastic boot. While single vertical, near vertical and near horizontal ventilation ports have been illustrated within the sides and dorsum flap portions of the liner 14, FIG. 3, the number of ventilation ports or windows, orientation of the same, as well as the length and width may be readily varied to complement and effect ventilation air movement throughout the ventilation system as created by the overlapping ventilation ports or windows within respective components 14, 12.

Additional features have been incorporated in the walker, and particularly the liner 4 of such walker to overcome problems which have developed in utilizing walkers such as that of U.S. Pat. No. 5,370,133. It has been found that after wearing the liner for a significant time, the hook-type VELCRO® material on the closing surface front of the liner and that at the top of the foot flaps no longer fasten well. As seen in FIG. 3, spaced loop-type VELCRO® patches 50 may be adhesively fixed to the outer surface as seen to the right side flap 36 and to the right side of the vertical portion of the foam liner 14, thereby effecting a more secure closure of the open front L-shaped enclosure.

Further, where loose foam pads are supplied with the walker to place over the ankles or about the ankle bone, or other pressure points, they have a tendency to slip even with the L-shaped enclosure liner secured in place about the leg and foot of the user. In FIG. 3, rectangular ankle bone pads 52 illustrated in dotted line are attached via hook-type VELCRO® fastener strips (not shown) which frictionally and mechanically attach directly to the inner surface layer of cloth of liner 14, positioned at a level to face the ankle bone of the user on respective sides thereof. To prevent liner slippage within the walker as illustrated in FIGS. 1 and 2, hook and loop type VELCRO® patches 54, 56 are respectively applied to the outer surface of the liner 14 at the rear of the L-shaped enclosure, FIG. 3, and the inside surface of the boot 12, FIG. 1, at corresponding same level positions for face-to-face frictional and mechanical engagement.

The major complaint of the patient's or user's wearing walkers is that they are extremely hot, even where open pore foam is employed. There is excessive heat built-up and perspiration caused by the heat, much to the discomfort of the user. This major complaint of heat is alleviated by the use of mesh covered windows. The liner 14 of FIG. 3 is different from that shown in FIG. 2 in U.S. Pat. No. 5,370,133. In the one-piece L-shaped enclosure of the '133 patent, it has been found that the foot does not fit well in the bottom of the liner, particularly where an insole may be required to be placed in the foot portion of the liner, as it is not shaped to accept such insole. The solution to this problem was the utilization of a separate foot portion 58 of the liner which is sewn in to provide a better fit for the foot and to accommodate insoles or materials such as PLASTAZOTE™ to accommodate plantar lesions of the foot. The invention, therefore, is limited solely by the claims appended hereto.

What is claimed is:

1. In a lower leg, ankle and foot immobilization brace preventing torsion of the lower leg, ankle and foot of a limb of the user while preventing dorsiflexion and plantar flexion of an ankle joint comprising:

a generally rigid walker sole;

a semi-flexible open front boot fixedly attached to the top of the walker sole;

at least one elongated ventilation port in the boot;

a foam liner within said boot surrounding the lower leg, ankle, foot and dorsum of the user;

closure means spanning the open front boot for applying general and focal compression to said foam liner encased limb of the user over the lower leg, ankle and dorsum thereby minimizing edema induced swelling over the full extent of the boot;

the improvement comprising:

at least one elongated ventilation port within said foam liner in a position for overlapping of said at least one elongated ventilation port in said boot to facilitate cooling air flow directly from the boot exterior onto the skin of the user's limb encased by the foam liner and exposed through said at least one elongated ventilation port within said foam liner.

2. The immobilization brace as claimed in claim 1, wherein said boot has a foot portion directly overlying said walker sole and a boot upper fixed to and extending above the foot portion proximate to said user's ankle, and wherein said at least one elongated ventilation port of said boot comprises vertically spaced, generally horizontal elongated ventilation ports within said boot upper, and said at least one elongated ventilation port within said liner comprises at least one elongated, generally vertical port within said liner in a portion surrounded by said boot upper and extending along a line so as to intersect a line passing through given ones of said plurality of elongated ventilation ports within said boot upper.

3. The immobilization brace as claimed in claim 2, wherein said plurality of elongated ventilation ports within said boot includes a plurality of spaced, generally horizontal elongated ventilation ports within said boot foot portion, and wherein said liner includes at least one generally horizontal, elongated ventilation port within a portion of said liner overlying the dorsum of the user's limb and along a line intersecting at least given ones of said boot foot portion ventilation ports.

4. The immobilization brace as claimed in claim 1, wherein said boot has a foot portion directly overlying said walker sole, and a boot upper fixed to and extending above the foot portion at a position proximate to said user's ankle, and wherein said at least one elongated ventilation port within said boot comprises a plurality of spaced, generally horizontal elongated ventilation ports within said boot foot portion, and wherein said liner includes at least one generally horizontal, elongated ventilation port within a foot portion of said liner overlying the dorsum of the user's limb and along a line intersecting at least given ones of said boot foot portion ventilation ports.

5. The immobilization brace as claimed in claim 1, wherein said foam liner is formed of an open pore foam material sheet.

6. The immobilization brace as claimed in claim 5, wherein said open pore foam material sheet is covered on opposite faces by porous cloth.

7. The immobilization brace as claimed in claim 1, wherein said at least one elongated ventilation port within said liner further include a binding ribbon extending about edges of said port bound by stitching.

8. The immobilization brace as claimed in claim 1, wherein said at least one elongated ventilation port within said liner is covered by loose woven material fixed to the periphery of said liner about said at least one elongated ventilation port on the surface of the foam liner contacting the skin of the user's limb to keep soft tissue of the limb from pushing through the at least one elongated ventilation port of said liner in case of edema without materially interfering with the escape of heat from the exposed foot and/or leg, while allowing ambient air to circulate through the vented area defined by overlapping elongated ventilation ports of said boot and liner.

9. A vented foam liner for use in a lower leg, ankle and foot immobilization brace preventing torsion of the lower leg, ankle and foot of a limb of a user while preventing dorsiflexion and plantar flexion of an ankle joint, said brace comprising:

a generally rigid walker sole;

a semi-flexible open front boot fixedly attached to the top of the walker sole;

at least one elongated ventilation port in the boot;

said vented foam liner being positionable within the boot surrounding the lower leg, ankle, foot and dorsum of the user's limb, and said semi-flexible boot comprises closure means spanning the open front boot for applying general and focal compression to said foam liner encased limb of the user over the lower leg, ankle and dorsum thereby minimizing edema induced swelling over the full extent of the boot;

the improvement wherein said foam liner includes at least one elongated ventilation port within said foam liner in a position generally overlapping said at least one elongated ventilation port in said boot to facilitate cooling air flow directly from the boot exterior to the skin of the user's limb encased by the foam liner and open to said at least one elongated ventilation port within said foam liner.

10. The vented foam liner as claimed in claim 9, wherein said at least one elongated ventilation port in said boot comprises a plurality of spaced ventilation ports and the liner is formed of molded foam sheet material cut and edge sealed together to form an L-shaped enclosure in side elevation to receive the lower leg, ankle and foot of the user, and wherein said at least one elongated ventilation port within said liner comprises a vertical elongated ventilation port within the vertical portion of the L-shaped enclosure positioned so as to overlap a plurality of vertically spaced, generally horizontal elongated ventilation ports within said semi-flexible boot.

11. The vented foam liner as claimed in claim 9, wherein said at least one elongated ventilation port within said foam liner comprises at least one generally horizontal elongated ventilation port within a horizontally extending foot portion of said L-shaped enclosure and positioned therein so as to overlap given ones of a plurality of elongated ventilation ports within the boot.

12. The vented foam liner as claimed in claim 9, wherein said liner is of open pore foam sheet material with cloth layers on opposite faces of said L-shaped enclosure walls, and wherein the exposed edge of said at least one elongated ventilation port within said foam liner has a stitched ribbon along said edge to prevent raveling of the cloth layers on opposite faces of the open pore foam material sheet forming said L-shaped enclosure.

13. The vented foam liner as claimed in claim 12, wherein said L-shaped enclosure includes L-shaped foam liner sheet portions, each including an elongated, vertical ventilation port within the vertical portion of the L-shaped enclosure and an elongated horizontal ventilation port within the horizontally projecting portion of said L-shaped enclosure for each of the two sides of the enclosure.

14. The vented foam liner as claimed in claim 9, wherein said at least one elongated ventilation port within said liner is covered by loose woven material fixed to the periphery of said liner about said at least one elongated ventilation port on the surface of the foam liner contacting the skin of the user's limb to keep soft tissue of the limb from pushing through the at least one elongated ventilation port of the liner in case of edema without materially interfering with the escape of heat from the exposed foot and/or leg, while allowing ambient air to circulate through the vented area defined by overlapping elongated ventilation ports of said boot and liner.

* * * * *